United States Patent
Menard et al.

(10) Patent No.: US 6,838,451 B1
(45) Date of Patent: Jan. 4, 2005

(54) METHODS AND COMPOSITIONS FOR THE PREVENTION AND TREATMENT OF INFLAMMATION, OSTEOARTHRITIS, AND OTHER DEGENERATIVE JOINT DISEASES

(75) Inventors: Michael Menard, Gurnee, IL (US); Susie Rockway, Grayslake, IL (US)

(73) Assignee: Pharmanutrients, Lake Bluff, IL (US)

( * ) Notice: Subject to any disclaimer, the term of this patent is extended or adjusted under 35 U.S.C. 154(b) by 0 days.

(21) Appl. No.: 10/333,295

(22) PCT Filed: Aug. 2, 2000

(86) PCT No.: PCT/US00/21046
§ 371 (c)(1),
(2), (4) Date: Jul. 3, 2003

(87) PCT Pub. No.: WO02/09725
PCT Pub. Date: Feb. 7, 2002

(51) Int. Cl.$^7$ .................. A61K 31/201; A61K 31/375; A61K 31/7008
(52) U.S. Cl. .................. 514/62; 514/474; 514/560
(58) Field of Search .................. 514/62, 474, 560

(56) References Cited

U.S. PATENT DOCUMENTS

| | | | |
|---|---|---|---|
| 4,981,844 A | | 1/1991 | Alexander et al. |
| 5,364,846 A | * | 11/1994 | Lang et al. .................. 514/102 |
| 5,587,363 A | * | 12/1996 | Henderson .................. 514/54 |
| 5,603,959 A | | 2/1997 | Horrobin et al. |
| 5,886,037 A | | 3/1999 | Klor et al. |
| 5,888,514 A | * | 3/1999 | Weisman .................. 424/94.1 |
| 6,060,514 A | | 5/2000 | Jerome et al. |

FOREIGN PATENT DOCUMENTS

WO    WO 99/29317    6/1999

OTHER PUBLICATIONS

U.S. Appl. No. 10/333,299, filed Jan. 17, 2003, Menard et al.
U.S. Appl. No. 10/333,297, filed Jan. 17, 2003, Menard et al.
U.S. Appl. No. 10/333,298, filed Jan. 17, 2003, Menard et al.
U.S. Appl. No. 10/333,295, filed Jan. 17, 2003, Menard et al.

* cited by examiner

*Primary Examiner*—James O. Wilson
*Assistant Examiner*—Ganapathy Krishnan
(74) *Attorney, Agent, or Firm*—Bell, Boyd & Lloyd LLC

(57) ABSTRACT

Methods and compositions for preventing and/or treating degenerative joint diseases including osteoarthritis as well as inflammation of the joints and for diminishing associated pain are provided. The formulation includes glucosamine, conjugated linoleic acid and ascorbic acid. Methods of treatment are also provided. The compositions and methods can be provided as an over-the-counter drug, a nutritional supplement, a prescription medication or component thereof, or a functional or medical food or component thereof.

25 Claims, No Drawings

METHODS AND COMPOSITIONS FOR THE PREVENTION AND TREATMENT OF INFLAMMATION, OSTEOARTHRITIS, AND OTHER DEGENERATIVE JOINT DISEASES

BACKGROUND OF THE INVENTION

The present invention relates generally to methods of treatment and products for treating disorders. More specifically, the present invention relates to methods and compositions for preventing, treating or providing relief from inflammation of the joints, osteoarthritis, and other degenerative joint diseases, or from pain associated with these conditions.

Inflammation of the joint is a common disorder. One result of such chronic inflammation, osteoarthritis (osteoarthrosis), is a degenerative process that is a major cause of invalidism in the adult population. Osteoarthritis is the most common form of all articular disorders, and first appears asymptomatically in the second or third decades and becomes almost universal by age 70. Almost all persons by the age of 40 have some pathological changes in weight bearing joints, although relatively few people are symptomatic. See *Merck Manual,* 16 Edition, page 1339.

The etiology of osteoarthritis is unknown. It appears to be the result of a complex system of interacting mechanical, biological, biochemical, and enzymatic feedback loops. When one or more of these systems fails, the clinical events follow. Many mechanisms can initiate the cellular and tissue events that constitute a final common pathway. Such mechanisms include: congenital joint abnormalities; genetic defects; infectious, metabolic, endocrine, and neuropathic diseases; virtually any disease process that alters the normal structure and function of hyaline cartilage; and acute or chronic trauma to the hyaline cartilage or tissue surrounding same. *Merck Manual,* id.

Analgesics and anti-inflammatory agents are used to attempt to manage this disorder. However, they do not stop or slow down the underlying degenerative process, they only function to relieve the pain. Although such nonsteroidal anti-inflammatory drugs have classically been used to alleviate pain and enhance joint movement associated with osteoarthritis and rheumatoid arthritis, their use is unfortunately associated with accelerated cartilage degeneration. The cartilage degeneration is due to the pathological effects of IL-1, EL-6, TNF, and PGF2, mediators of the acute phase response. The combined effects of these catabolic agents upset the delicate homeostatic balance between synthesis, repair, and degradation of cartilage.

There is a need for improved compositions and methods for treating degenerative joint disease such as osteoarthritis.

SUMMARY OF THE INVENTION

Pursuant to the present invention, methods and compositions for preventing and treating degenerative joint diseases including osteoarthritis as well as inflammation of the joints, as well as associated pain are provided. The formulation includes glucosamine, conjugated linoleic acid, and ascorbic acid. Methods of treatment are also provided. The compositions and methods can be provided as an over-the-counter drug, a nutritional supplement, or a prescription medication or component thereof, or as a component of functional or medical foods.

To this end the present invention provides a method for preventing or treating degenerative joint disease comprising the step of administering a therapeutically effective amount of a composition comprising conjugated linoleic acid, glucosamine, and ascorbic acid.

In an embodiment, approximately 0.5 to about 10.0 grams per day of conjugated linoleic acid are administered.

In an embodiment, approximately 500 mg to about 2500 mg per day of glucosamine is administered. Preferably 1500 mg to 2500 mg per day.

In an embodiment, approximately 50 mg to about 500 mg per day of ascorbic acid is administered. Preferably 100 mg to 400 mg per day.

In an embodiment, the conjugated linoleic acid is either a pure isomer of octadecadienoic acid, or a mixture of octadecadienoic acid isomers selected from the group consisting of: cis-8, cis-10; cis-8, trans-10; trans-8, cis 10; trans-8, trans-10; cis-9, cis-11; cis-9, trans-11; trans-9, cis-11; trans-9, trans-11; cis-10, cis-12; cis-9, trans-12; trans-9, cis-12; trans-10, trans-12; cis-11, cis-13; cis-11, trans-13; trans-11, cis-13; trans-11, trans-13 octadecadienoic acid; metabolites thereof, including but not limited to 18:3 cis-6, cis-9, trans-11; 18:3 cis-6, trans-10, cis-12; 18:3 cis-8, trans-12, cis-14; 20:3 cis-8, cis-11, trans-13; 20:4 cis-5, cis-8, cis-11, trans-13; 20:4 cis-5, cis-8, trans-12, cis-14; as well as precursors or derivatives thereof.

In an embodiment, the composition includes a flavor.

In an embodiment, the composition includes an artificial sweetener.

In an embodiment, the composition is in pill form.

In an embodiment, the degenerative joint disease is osteoarthritis. In an embodiment, the degenerative joint disease is rheumatoid arthritis, or associated disorders.

In a further embodiment of the present invention, a composition is provided comprising a therapeutically effective amount of conjugated linoleic acid, glucosamine, and ascorbic acid.

In an embodiment, the composition comprises approximately 14% to about 87% by weight conjugated linoleic acid.

In an embodiment, the composition comprises approximately 12% to about 82% by weight glucosamine.

In an embodiment, the composition comprises approximately 0.1% to about 20% by weight ascorbic acid.

In yet another embodiment of the present invention, a method of treating inflammation of the joints is provided comprising the step of administering a therapeutically effective amount of a composition comprising conjugated linoleic acid, glucosamine, and ascorbic acid.

It is an advantage of the present invention to provide a composition for treating inflammation of the joints.

Another advantage of the present invention is to provide a composition and method for treating osteoarthritis and other degenerative joint diseases.

Still further, an advantage of the present invention is to provide a product that can reduce the damaging degenerative process involved in joint disease.

Further, an advantage of the present invention is to provide a product and method that can reverse the damaging degenerative process involved in joint disease.

Moreover, an advantage of the present invention is to provide a composition and method for reducing the debilitating pain associated with joint disease.

Furthermore, an advantage of the present invention is to provide a composition and method for increasing mobility in patients with degenerative joint disease.

A further advantage of the present invention is to provide a composition and method for alleviating the chronic catabolic stress response associated with degenerative joint disease.

Still, an advantage of the present invention is to provide a composition and method for reducing inflammatory response associated with joint discomfort.

Additionally, an advantage of the present invention is to provide a composition and method for enhancing cartilage synthesis and/or preventing or minimizing cartilage degradation, thus promoting cartilage repair mechanisms.

Additional features and advantages of the present invention will be described in and apparent from the detailed description of the presently preferred embodiments.

DETAILED DESCRIPTION OF THE PRESENTLY PREFERRED EMBODIMENTS

Pursuant to the present invention, methods and compositions for treating degenerative joint diseases including osteoarthritis as well as inflammation of the joints are provided. The formulation includes glucosamine, conjugated linoleic acid, and ascorbic acid. Methods of treatment are also provided. The composition and method can be provided as an over-the-counter drug, a nutritional supplement, or a prescription medication.

Glucosamine is a component of all human tissue and is found in especially high concentrations in the cartilage. Chemically an aminomonosaccharide, glucosamine provides the building blocks for the O-linked and N-linked glycosaminoglycans comprising the matrix of the connective tissues in the body. The sulfate form is readily absorbed from the small intestine—over 90%. Of the absorbed glucosamine, 25% will be excreted in the urine, 65% excreted as exhaled carbon dioxide, and 10% remaining in the tissues. Once it is taken up into the chondrocytes of cartilage, glucosamine is incorporated into proteoglycans. There have been no reports of significant drug interactions of glucosamine with antibiotics or antidepressants.

Vitamin C is an essential vitamin with an RDI of 60 mg per day. The deficiency of this vitamin is associated with poor wound healing, most likely due to poor collagen synthesis. This water-soluble vitamin is not usually stored, thus, there is little evidence of toxicity.

Current evidence suggests that pro-inflammatory cytokines are responsible for the catabolic process occurring in the pathological tissues. In addition to other cataboic mediators, these pro-inflammatory mediators, particularly interleukins (IL-1, EL-6), and tumor necrosis factor (TNF)-α, are major catabolic compounds involved in the destruction of joint tissues. In the inflammatory response of osteoarthritic articular cells, the changes in cyclooxygenase-2 (COX-2) expression and/or activity seems one of the major determinants for prostaglandin ($PGE_2$) production. Chondrocytes are highly sensitive to IL-1 and it appears this cytokine inhibits repair and regeneration of extracellular matrix and increases catabolic activity of the mate. Speculation is that immunological mediators (humoral and locally produced) play a primary role in skeletal muscle remodeling and perhaps cartilage remodeling as well. Thus, it appears necessary to modify this catabolic event to retard and/or reverse the breakdown of cartilage.

Conjugated linoleic acid refers to a group of di- and tri-enoic derivatives of linoleic acid that occur naturally in milk and meat of ruminating animals. It can be synthesized in the laboratory and is available commercially as a dietary supplement and has been shown to be nontoxic.

Pursuant to the present invention, conjugated linoleic acid can be conjugated linoleic acid such as that set forth in U.S. Pat. No. 5,986,116 the disclosure of which is incorporated herein by reference.

Conjugated linoleic acid appears to modulate the immune system under conditions where COX-2 enzyme is induced by suppressing PGE-2 production. The mechanism for the observed anti-inflammatory effects of conjugated linoleic acid in various animal models has been associated with reduced arachidonic acid, a precursor for PGE, accumulation in cell membranes. Any effect conjugated linoleic acid has on the synthesis of eicosanoids should correlate with the uptake of conjugated linoleic acid into neutral phospholipids by cells. Conjugated linoleic acid can be readily incorporated in a dose-dependent manner into the tissues of animals consuming diets containing conjugated linoleic acid and a concomitant reduction of arachidonic acid.

Human articular cartilage is highly specialized tissue, composed of chondrocytes embedded in an extracellular matrix. The matrix contains fibrillar components consisting mainly of collagen proteins, and non-fibrillar components, made up of proteoglycans, hyaluronic acid and water. Proteoglycan subunits consist of glycosaminoglycans (chondroitin and keratin sulfates) surrounding a protein core. Cartilage metabolism involves processes of synthesis, repair and degradation, which are ongoing and mediated by chondrocytes. When the balance among these processes is upset as in osteoarthritis and rheumatoid arthritis, cartilage damage results. The breakdown of the cartilage matrix is believed to be due to locally produced IL-1 from inflammatory cells increasing catabolic activity in adjacent chondrocytes. Thus, CLA may inhibit catabolic response while oral glucosamine stimulates the manufacture of substances necessary for proper joint function and stimulate joint repair.

Orally administered glucosamine sulfate is selectively taken up by the articular cartilage and stimulates the manufacture of glycosaminoglycan, a key structural component of cartilage. It also promotes the incorporation of sulfur into cartilage. Ascorbic acid acts as a reductive cofactor for post-translational hydroxylation of peptide bound proline and lysine residues during formation of collagen. These hydroxylated amino acids allow cross-linking which stabilizes the triple helical structure of tropocollagen, an essential subunit of procollagen. Ascorbic acid may be involved in gene regulation of collagen synthesis and mRNA processing. In addition, ascorbic acid influences cellular procollagen secretion and biosynthesis of other connective tissue components such as elan proteoglycans and bone matrix. Ascorbic acid is also involved with various immune-related functions such as neutrophil chemotaxis, lymphocyte proliferation, antimicrobial and natural killer cell activities and may also modulate prostacyclin, prostaglandins, and B- and T-cell cyclic nucleotides. The mechanisms for these effects are not clearly resolved, nor the absolute amount of ascorbic acid needed to assist in these areas. Because the normal dietary intake of ascorbic acid in humans is often less than 60 mg set as the recommended daily intake (RDI), it appears prudent to add this important cofactor as an active ingredient in this unique formula. Inclusion of this essential vitamin may assist in promoting collagen formation and wound healing.

By way of example and not limitation, examples of the present invention will now be given.

Proposed Formulations:

Preferably, the product will comprise as active ingredients:

approximately 14% to about 87% by weight conjugated linoleic acid;

approximately 12% to about 82% by weight glucosamine SO$_4$; and approximately 0.5% to about 20% by weight ascorbic acid.

In a preferred embodiment, the product will comprise as active ingredients:

| | |
|---|---|
| conjugated linoleic acid | 45% |
| glucosamine SO$_4$ | 45% |
| ascorbic acid | 10% |

By way of example, it is envisioned that a dose of the product will comprise two tablets of conjugated linoleic acid/clucosamine sulfate/ascorbic acid. Each dose (two tablets) will contain:

| | |
|---|---|
| conjugated linoleic acid powder | 500 mg; |
| glucosamine SO$_4$ | 500 mg; and |
| ascorbic acid | 100 mg. |

The tablets may include the following excipients and flavorings: magnesium stearate, silicone dioxide, croscarmelose sodium, sterric acid, microcrystalline cellulose, calcium phosphate, aqueous base film coat.

By way of example and not limitation, contemplative examples of the present invention will now be given.

CONTEMPLATIVE EXAMPLE NO. 1

To treat osteoarthritis, a daily administration of formulation will be given in an amount to provide:

20 mg/kg/day conjugated linoleic acid to 100 mg/kg/day conjugated linoleic acid, 1500 mg/day glucosamine to 2500 mg/day glucosamine, and 100 mg/day ascorbic acid to 400 mg/day ascorbic acid.

CONTEMPLATIVE EXAMPLE NO. 2

To treat rheumatoid arthritis, a daily administration of formulation will be given in an amount to provide:

20 mg/kg/day conjugated linoleic acid to 100 mg/kg/day conjugated linoleic acid, 1500 mg/day glucosamine to 2500 mg/day glucosamine, and 100 mg/day ascorbic acid to 400 mg/day ascorbic acid.

CONTEMPLATIVE EXAMPLE NO. 3

To treat joint discomfort and pain, a daily administration of formulation will be given in an amount to provide:

20 mg/kg/day conjugated linoleic acid to 60 mg/kg/day conjugated linoleic acid, 1500 mg/day glucosamine to 2500 mg/day glucosamine, and 100 mg/day ascorbic acid to 400 mg/day ascorbic acid.

CONTEMPLATIVE EXAMPLE NO. 4

Prophylactic (Maintain Joint Health)

To maintain joint health a daily administration of formulation will be given in an amount to provide:

20 mg/kg/day conjugated linoleic acid to 60 mg/kg/day conjugated linoleic acid, 1500 mg/day glucosamine to 2500 mg/day glucosamine, and 100 mg/day ascorbic acid to 400 mg/day ascorbic acid.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

We claim:

1. A method for treating arthritis, osteoarthritis, or joint pain comprising the step of administering to an animal a therapeutically effective amount of a composition comprising conjugated linoleic acid, glucosamine, and ascorbic acid.

2. The method of claim 1 wherein approximately 0.5 to about 10 grams per day of conjugated linoleic acid are administered.

3. The method of claim 1 wherein approximately 1500 mg to about 2500 mg per day of glucosamine is administered.

4. The method of claim 1 wherein approximately 100 mg to about 400 mg per day of ascorbic acid is administered.

5. The method of claim 1 wherein the conjugated linoleic acid is selected from the group consisting of: a pure isomer of octadecadienoic acid; mixtures of octadecadienoic acid isomers: cis-8, cis-10; cis-8, trans-10; trans-8, cis-10; trans-8, trans-10; cis-9, cis-1; cis-9, trans-11; trans-9, cis-11; trans-9, trans-11; cis-16, cis-12; cis-9 trans-12; trans-9, cis-12; trans-10-trans-12; cis-11, cis-13; cis-11, trans-13; trans-11, cis-13; octadecadienoic acid.

6. The method of claim 1 wherein the composition includes a flavor.

7. The method of claim 1 wherein the composition includes an artificial sweetener.

8. The method of claim 1 wherein the composition is in pill form.

9. The method of claim 1 wherein the degenerative joint disease is osteoarthritis.

10. A composition comprising a therapeutically effective amount of conjugated linoleic acid, glucosamine, and ascorbic acid.

11. The composition of claim 10 wherein approximately 14% to about 87% by weight of the composition is conjugated linoleic acid.

12. The composition of claim 10 wherein approximately 12% to about 82% by weight of the composition is glucosamine.

13. The composition of claim 10 wherein approximately 0.5% to about 20% by weight of the composition is ascorbic acid.

14. The composition of claim 10 wherein the conjugated linoleic acid is selected from the group consisting of: a pure isomer of octadecadienoic acid; mixtures of octadecadienoic acid isomers: cis-8, cis-10; cis-8, trans-10; trans-8, cis-10; trans-8, trans-10; cis-9, cis-11; cis-9, trans-11; trans-9, cis-11; trans-9, trans-11; cis-10, cis-12; cis-9 trans-12; trans-9, cis-12; trans-10-trans-12; cis-1, cis-13; cis-11, trans-13; trans-11, cis-13; trans-11, trans-13 octadecadienoic acid.

15. The composition of claim 10 wherein the composition includes a flavor.

16. The composition of claim 10 wherein the composition includes an artificial sweetener.

17. The composition of claim 10 wherein the composition is in pill form.

18. A method of treating inflammation of the joints comprising the step of administering to an animal a therapeutically effective amount of a composition comprising conjugated linoleic acid, glucosamine, and ascorbic acid.

19. The method of claim 18 wherein approximately 0.5 to about 10 grams per day of conjugated linoleic acid are administered.

20. The method of claim 18 wherein approximately 1500 mg to about 2500 mg per day of glucosamine is administered.

21. The method of claim 18 wherein approximately 100 mg to about 400 mg per day of ascorbic acid is administered.

22. The method of claim 18 wherein the conjugated linoleic acid is selected from the group consisting of: a pure isomer of octadecadienoic acid; mixtures of octadecadienoic acid isomers: cis-8, cis-10; cis-8, trans-10; trans-8, cis-10; trans-8, trans-10; cis-9, cis-11; cis-9, trans-11; trans-9, cis-11; trans-9, trans-11; cis-10, cis-12; cis-9 trans-12; trans-9, cis-12; trans-10-trans-12; cis-11, cis-13; cis-11, trans-13; trans-11, cis-13; trans-11, trans-13 octadecadienoic acid.

23. The method of claim 18 wherein the composition includes a flavor.

24. The method of claim 18 wherein the composition includes an artificial sweetener.

25. The method of claim 18 wherein the composition is in pill form.

* * * * *

UNITED STATES PATENT AND TRADEMARK OFFICE
CERTIFICATE OF CORRECTION

PATENT NO. : 6,838,451 B1
DATED : January 4, 2005
INVENTOR(S) : Michael Menard and Susie Rockway It is certified that error appears in the above-identified patent and that said Letters Patent is hereby corrected as shown below:

Column 4,
Line 38, please insert a new paragraph before "Ascorbic."

Column 6,
Line 23, please change "cis-1" to -- cis- 11 --.
Line 24, please change "cis-16" to -- cis- 10 --.
Line 26, after "cis-13;" please insert -- trans-11, trans-13 --.
Line 53, please change "cis-1" to -- cis- 11 --.

Signed and Sealed this

Seventh Day of June, 2005

JON W. DUDAS
*Director of the United States Patent and Trademark Office*